(12) United States Patent
Huo et al.

(10) Patent No.: US 6,472,215 B1
(45) Date of Patent: Oct. 29, 2002

(54) METHOD OF ANALYZING NUCLEATED RED BLOOD CELLS IN A BLOOD SAMPLE

(75) Inventors: Ziling Huo, Miami, FL (US); Jaesang Park, Miami, FL (US); Wei Yao, Miami, FL (US); Shuliang Zhang, Miami, FL (US); Min Zheng, Pembroke Pines, FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/917,450

(22) Filed: Jul. 27, 2001

(51) Int. Cl.[7] .............................................. G01N 31/00
(52) U.S. Cl. ............................ 436/10; 436/8; 436/17; 436/63; 436/149; 436/150; 436/164; 422/73; 422/82.01; 422/82.02; 422/82.09; 435/2; 435/29; 435/34
(58) Field of Search ............................... 436/8, 10, 17, 436/18, 63, 149, 150, 164, 175; 252/408.1; 435/2, 4, 29, 34; 422/73, 82.01, 82.02, 82.05, 82.09

(56) References Cited

U.S. PATENT DOCUMENTS

| | | | |
|---|---|---|---|
| 2,656,508 A | 10/1953 | Coulter | |
| 4,528,274 A | 7/1985 | Carter et al. ................... | 436/10 |
| 4,962,038 A | 10/1990 | Carter et al. ................... | 436/10 |
| 5,040,112 A | 8/1991 | Marshall et al. ........ | 364/413.08 |
| 5,125,737 A | 6/1992 | Rodriguez et al. ............. | 356/39 |
| 5,155,044 A | 10/1992 | Ledis et al. .................... | 436/17 |
| 5,298,426 A | 3/1994 | Inami et al. .................... | 436/63 |
| 5,516,695 A * | 5/1996 | Kim et al. ....................... | 435/2 |
| 5,559,037 A | 9/1996 | Kim et al. ....................... | 436/63 |
| 5,648,225 A | 7/1997 | Kim et al. .................. | 435/7.24 |
| 5,686,308 A | 11/1997 | Li et al. ......................... | 436/63 |
| 5,834,315 A | 11/1998 | Riesgo et al. .................. | 436/66 |
| 5,874,310 A | 2/1999 | Li et al. ......................... | 436/10 |
| 5,879,900 A | 3/1999 | Kim et al. .................. | 435/7.24 |
| 5,917,584 A | 6/1999 | Li et al. ......................... | 356/39 |
| 5,935,857 A | 8/1999 | Riesgo et al. .................. | 436/18 |
| 6,228,652 B1 * | 5/2001 | Rodriguez et al. ........... | 356/335 |
| 6,410,330 B1 * | 6/2002 | Li et al. ......................... | 422/73 |

FOREIGN PATENT DOCUMENTS

EP    1 004 880 A2    5/2000

* cited by examiner

Primary Examiner—Maureen M. Wallenhorst
(74) Attorney, Agent, or Firm—Mitchell E. Alter

(57) ABSTRACT

A method of analyzing nucleated red blood cells (NRBCs) in a blood sample and further enumerating NRBCs is disclosed. The method includes lysing a first aliquot and a second aliquot of a blood sample separately with a first lysing reagent system and a second lysing reagent system; measuring the first sample mixture in a flow cell by DC, RF, and light scatter measurements; measuring cell distributions and counting remaining blood cells in the second sample mixture by DC impedance measurements in a non-focused flow aperture; analyzing blood cell distribution patterns obtained from measuring the first sample mixture and from measuring the second sample mixture respectively; and further performing a combined analysis to differentiate NRBCs from other cell types and determine numbers of NRBCs in the blood sample.

19 Claims, 4 Drawing Sheets

METHOD OF ANALYZING NUCLEATED RED BLOOD CELLS IN A BLOOD SAMPLE

FIELD OF THE INVENTION

The present invention relates to a method of analyzing nucleated red blood cells in a blood sample. More specifically the method analyzes blood cell distribution patterns obtained from two separate blood measurement results, determines the presence of nucleated red blood cells, and further enumerates nucleated red blood cells in a blood sample.

BACKGROUND OF THE INVENTION

Normal peripheral blood contains mature red blood cells which are free of nucleus. Nucleated red blood cells (NRBCs), also known as erythroblasts, are immature red blood cells. They normally occur in the bone marrow but not in peripheral blood. A presence of a significant number of NRBCs in peripheral blood may reflect a disturbance of red blood cell maturation, such as megaloblastic anemia, hemolytic conditions including thalassemia, sickle cell crises, leukemia, and transfusion reactions. Therefore, it is of clinical importance to measure NRBCs. Traditionally, differentiation and enumeration of NRBC are performed manually. The process involves the smearing of a blood sample on a microscope slide and staining the slide, followed by manual visual analysis of the individual slide. The NRBC concentration is reported as numbers of NRBC per 100 white blood cells. Usually, 200 white blood cells and the numbers of NRBC present in the same region on a blood smear are counted and the numbers are divided by 2 to express the NRBC concentration as the numbers of NRBC/100 WBC. This approach is extremely time-consuming as well as being subjective to the interpretation of the individual analyzing the slide.

In recent years, several fluorescence flow cytometry methods have been developed for differentiating NRBCs. These methods utilizes specific nuclear staining technique to distinguish NRBCs from other cell types because it is difficult to differentiate NRBCs based on their electronic or optical properties.

U.S. Pat. No. 5,298,426 (to Inami et al.) discloses a fluorescence method for differentiating NRBCs. The method utilizes a two-step staining using a first fluid and a second fluid. Inami et al. teaches that the first fluid contains an erythroblast-staining dye that diffuses into nucleated red blood cells to specifically stain their nuclei, and then separating a group of NRBCs from other cell groups on a two-dimensional plot whereby the results of NRBC differentiation are computed. In order to differentiate leukocyte subpopulation concurrently, the first fluid also contains two additional fluorescence dyes, i.e., an eosinophil/basophil-staining dye and leukocyte-staining dye for specific staining of these cell types.

U.S. Pat. No. 5,559,037 (to Kim et al.) discloses a method for flow cytometric analysis of NRBCs and leukocytes. The method comprises lysis of red blood cells and NRBC cytoplasm from a whole blood sample to expose the NRBC nuclei to a vital nuclear stain and minimizing the permeation of the vital nuclear stain into the leukocytes and analyzing the sample by measuring fluorescence and two angles of light scatter. This method features a triple triggering method which blocks the signals from debris (fluorescent and non-fluorescent) and identifies the signals which fall below the ALL trigger but above the fluorescence trigger (FL3) as NRBCs. ALL is the axial loss of light or the light scatter signals detected at 0° from the incident light. Therefore, pre-gating signals in more than one dimension are required in this method for identification of NRBC population. Since leukocytes are also nucleated cells, staining of these cells needs to be prevented to avoid interference to the fluorescence measurement. The preservation of leukocyte membrane and minimizing the permeation of the nuclear stain into the leukocytes are achieved by concurrently fixing the leukocytes with an aliphatic aldehyde during lysis of red blood cells. In addition, the method requires heating of the reagent to 42° C. in order to obtain the NRBC and leukocyte differentiations.

U.S. Pat. No. 5,648,225 (to Kim et al) discloses a method of using a multipurpose lysing reagent for subclassification of nucleated blood cells. The method comprises the steps of lysing a blood sample with the multipurpose lysing reagent which contains a nuclear stain, incubating the sample mixture at an elevated temperature, and determining the nucleated blood cells including NRBCs with an automated electro-optical hematology instrumentation.

U.S. Pat. No. 5,879,900 (to Kim et al) discloses a method of differentiating NRBCs, damaged white blood cells (WBC), WBC and a WBC differential in a blood sample by flow cytometry. The method includes lysing a blood sample; staining NRBCs and any damaged white blood cells with a vital nuclear stain; analyzing the sample mixture by measuring at least one fluorescence, and at least one light scatter signals in a range from 0° to 1° and 3° to 10°; constructing a three-dimensional plot from the fluorescence and light scatter signals; and differentiating and enumerating WBC, NRBC, damaged WBC and a WBC subclass differential.

EP 1 004 880 A2 discloses reagents and a method for discrimination and counting of nucleated red blood cells. The method includes the steps of lysing red blood cells, staining white blood cells and NRBCs, assaying the sample by measuring at least one scattered light parameter, and at least one fluorescence parameter.

U.S. Pat. No. 5,874,310 (to Li et al) discloses a method for differentiation of nucleated red blood cells. The method includes lysing mature red blood cells and analyzing the sample in a flow cell by light scatter measurement to differentiate NRBCs from other cell types. The light scatter measurement is performed by using two low angle light scatter signals of less than 10°. The method further includes a concurrent differentiation of white blood cells using electronic and optical analysis, wherein the electronic analysis is a DC impedance measurement.

U.S. Pat. No. 5,917,584 (to Li et al) discloses a method for differentiation of nucleated red blood cells. The method includes lysing mature red blood cells in a blood sample; analyzing the sample in a flow cell by two angles of light scatter measurement to differentiate NRBCs from other cell types, wherein the first light scatter signal is a low angle light scatter signal of less than 10°, and the second light scatter signal is a medium angle or a right-angle light scatter signal.

The above described methods enable differentiation and enumeration of NRBCs and leukocytes by fluorescence flow cytometry and multi-angle light scatter measurements. However, fluorescence and multi-angle light scatter measurements are complex and expensive detection methods.

Many current automated hematology analyzers, such as Abbott Cell-Dyne® 3500, COULTER® GEN*S™, Bayer Advia*120®, and Sysmex™ NE-9000 are only able to provide NRBC flagging for the possible presence of NRBCs in an analyzed blood sample when the instruments sense an increased amount of signals near blood cell debris area of an obtained cell distribution histogram. However, these methods are prone to generate false positive flaggings because many other blood abnormalities can cause increased signals at the same area, such as platelet clumps and sickle cells, as well as cell debris from insufficiently lysed blood samples.

Furthermore, a known problem with NRBC containing samples is erroneous white blood cell count (WBC) reported by hematology analyzers on these samples. Since the nuclear volumes of NRBC are close to those of white blood cells, and they are commonly counted as white blood cells on hematology analyzers which measure the sizes of blood cells, resulting an elevation of WBC. Therefore, correction of NRBC contribution to the WBC reported from hematology analyzer is required for samples containing NRBCs. Current practice in clinical laboratory is to subtract the numbers of NRBC obtained by manual count from the WBC reported by the hematology analyzers. This is time consuming and error prone.

Therefore, there presents a need for a simple and less expensive measurement method for analyzing and enumerating NRBCs in a blood sample.

SUMMARY OF THE INVENTION

Figure 1A:
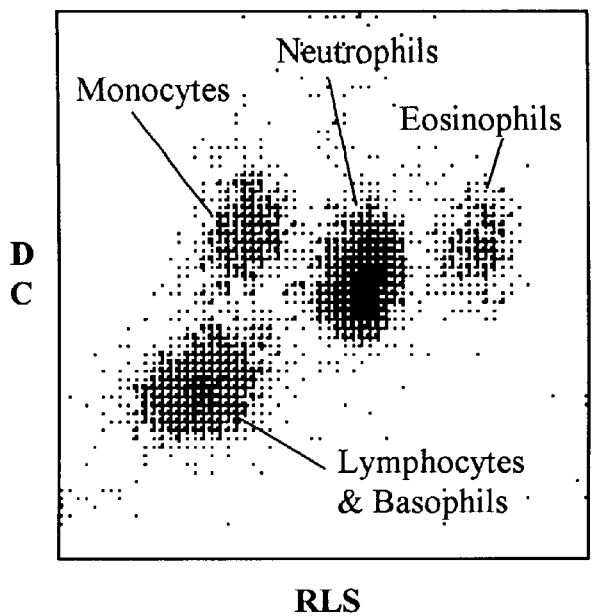
FIGS. 1A and 1B are the scattergrams obtained from the measurement of the first aliquot of a normal blood sample processed according to the procedure described in Example 1.

The present invention relates to a method of analyzing nucleated red blood cells in a blood sample. The method comprises the steps of: (a) exposing a first aliquot of a blood sample to a first lysing reagent system to lyse red blood cells and to form first sample mixture, (b) exposing a second aliquot of a blood sample to a second lysing reagent system to lyse red blood cells and to form second sample mixture; (c) measuring the first sample mixture in a flow cell by a detection comprising a direct current impedance measurement (DC1), radio frequency impedance measurement (RF), and light scatter measurement (LS); (d) measuring blood cell distributions of the second sample mixture by a second direct current impedance measurement (DC2) in a non-focused flow aperture; (e) analyzing blood cell distribution patterns obtained from measuring the first sample mixture, and differentiating nucleated red blood cells from other cell types; (f) analyzing blood cell distribution patterns obtained from measuring the second sample mixture, and differentiating nucleated red blood cells from other cell types; (g) performing a combined analysis on a profile obtained by combining results of analysis from step (e) and (f), the combined analysis further differentiating nucleated red blood cells from other cell types, and (h) reporting nucleated red blood cells in the blood sample. The method can report the presence of nucleated red blood cells in the blood sample, and can further report the amount of nucleated red blood cells as numbers of nucleated red blood cells per hundred white blood cells in the blood sample.

The method further comprises counting remaining blood cells in the second sample mixture in the non-focus flow aperture by a third direct current impedance measurement, and reporting numbers of white blood cells in an unit volume of the blood sample. Moreover the method further comprises reporting an amount of nucleated red blood cells as numbers of nucleated red blood cells in an unit volume of the blood sample.

DETAILED DESCRIPTION OF THE INVENTION

In one embodiment, the present invention is directed to a method for analyzing nucleated red blood cells (NRBCs) in a blood sample.

The method comprises the steps of (a) exposing a first aliquot of a blood sample to a first lysing reagent system to lyse red blood cells and to form a first sample mixture, (b) exposing a second aliquot of a blood sample to a second lysing reagent system to lyse red blood cells and to form a second sample mixture, (c) measuring the first sample mixture in a flow cell by direct current impedance measurement (DC1), radio frequency impedance measurement (RF), and light scatter measurement (LS), (d) measuring the second sample mixture by a second direct current impedance measurement (DC2) in a non-focused flow aperture, (e) analyzing blood cell distribution patterns obtained from measuring the first sample mixture, and differentiating nucleated red blood cells from other cell types, (f) analyzing blood cell distribution patterns obtained from measuring the second sample mixture, and differentiating nucleated red blood cells from other cell types, (g) performing a combined analysis on a profile obtained by combining results of analysis from step (e) and (f), the combined analysis further differentiating nucleated red blood cells from other cell types, and (h) reporting nucleated red blood cells in said blood sample.

The first lysing reagent system comprises a lytic reagent and a stabilizing reagent. A suitable example of the first lysing reagent system is a commercial product, SCATTER PAK®, manufactured by Beckman Coulter, Inc., Miami, Fla. This lysing reagent system has a hypotonic acidic lytic reagent, Erythrolyse II, and a hypertonic alkaline stabilizing reagent, StabiLyse™. The composition of the lysing reagent system and method of use for blood analysis are fully described in U.S. Pat. No. 5,155,044 (to Ledis et al.), which is hereby incorporated by reference in its entirety.

Another suitable example of the first lysing reagent system is described in U.S. Pat. No. 5,686,308 (to Li et al.), which is hereby incorporated by reference in its entirety.

To prepare the first aliquot of the blood sample for measurement, the method includes first mixing the first aliquot of the blood sample with a predetermined volume of the lytic reagent to lyse red blood cells, and subsequently adding the stabilizing reagent to retard further lytic reaction in the sample mixture. Using the first lysing reagent system described above, white blood cells in the sample mixture remain essentially intact, and can be used for a subsequent differential analysis. Nucleated red blood cells are more fragile, and their cell membranes are lysed under the same lysing condition. The NRBCs in the first sample mixture have much smaller volume than white blood cells.

The measurement of the first sample mixture is performed in a focused flow cell using direct current impedance (DC1), radio frequency impedance (RF), and light scatter measurements. When a particle, such as a blood cell, passes through the aperture of a flow cell, an electrical signal can be measured due to conductivity or impedance change. The electrical pulse shape, height and width, is directly related to the size of a particle or a blood cell, and can be converted to the size of the particles measured. The blood cell also scatters the incident light from a laser beam in all directions. The light scatter signals can be detected by a light detector at various angles relative to the incident light beam between 0° to 180°. It has been found that each cell population has different light scattering properties, either significant or minor, which might be utilized for differentiation of different cell populations. For the purpose of the present invention, light scatter signals between 10° and 70° are detected for the light scatter measurement. The light scatter signals in this range is also called median angle light scatter.

The DC and RF impedance measurement and median angle light scatter measurement device used with focused flow cell for blood cell analysis on an automated hematology analyzer is known to those skilled in the art, and is generally described in U.S. Pat. No. 5,125,737 (to Rodriguez et al.), which is hereby incorporated by reference in its entirety.

The DC1, RF and light scatter measurements made on the first sample mixture can produce a series of two dimensional scattergrams using the measured parameters or derivatives of the direct measurements.

Figure 1B:
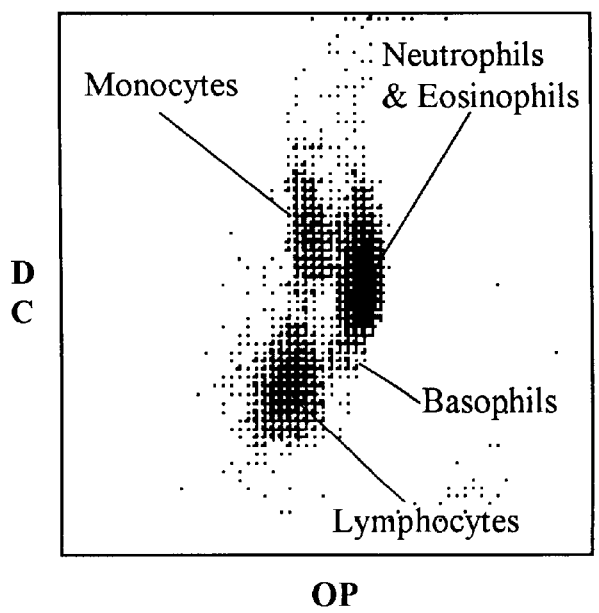

FIGS. 1A and 1B are scattergrams of DC1 versus a first transformed light scatter (RLS), and DC1 versus Opacity (OP, a function of DC1 and RF), respectively, obtained from a normal blood sample processed and analyzed following the procedure described in Example 1. As shown, white blood cells are separated into their subpopulations in the two scattergrams, including lymphocytes, monocytes, neutrophils, eosinophils, and basophils. Importantly, there is no blood cell population in the region below lymphocytes.

Figure 2A:
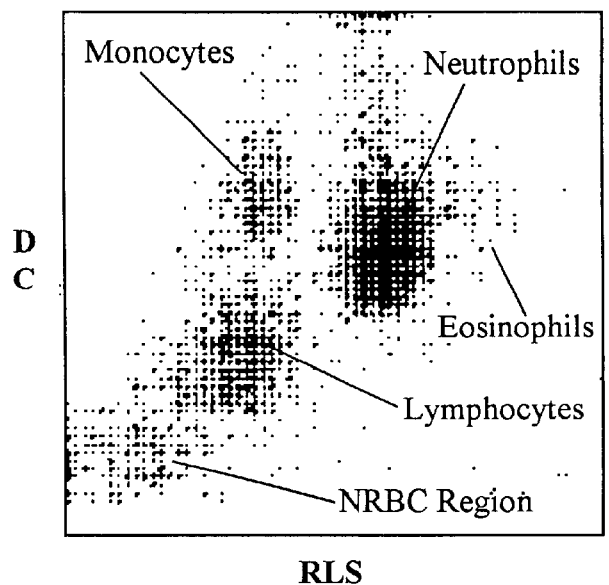
FIGS. 2A and 2B are the scattergrams obtained from the measurement of the first aliquot of a clinical blood sample containing NRBCs as described in Example 2.
Figure 2B:
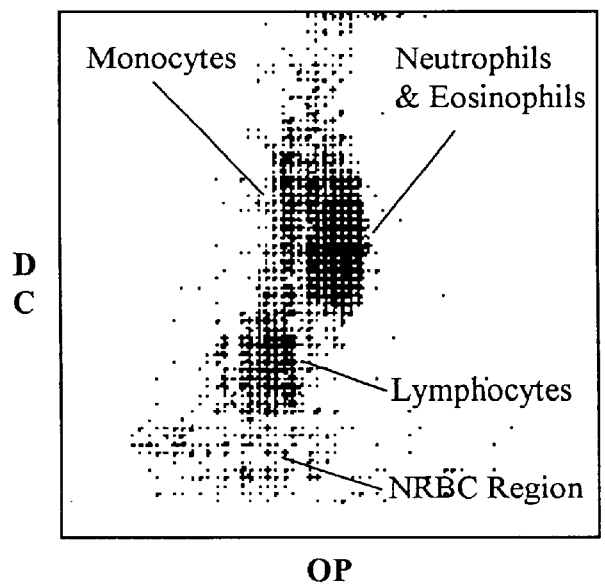
Figure 2C:
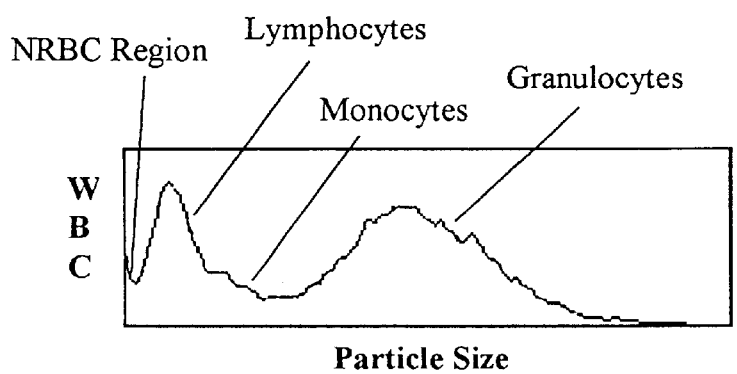
FIG. 2C is a DC2 histogram obtained from the measurement of the second aliquot of the same clinical sample.

FIGS. 2A and 2B are two scattergrams in the same dimensions to those in FIGS. 1A and 1B, respectively, obtained under the same condition from a clinical sample that has 5 NRBCs/100 WBC. In this case, NRBCs appear in the region below the lymphocytes in the DC1 scale.

The second lysing reagent system comprises a blood diluent, and a second lytic reagent. Suitable examples of the blood diluent are commercial products, ISOTON® and ISOTON® 4. Suitable examples of the second lytic reagent are commercial products, LYSE S® III Diff and LYSE S® 4. These reagents are manufactured by Beckman Coulter, Inc. Miami, Fla. The second lysing reagent system and method of use for blood analysis are fully described in U.S. Pat. No. 4,528,274 (to Carter et al.) and U.S. Pat. No. 4,962,038 (to Carter et al.), U.S. Pat. No. 5,834,315 (to Riesgo et al.), and U.S. Pat. No. 5,935,857 (to Riesgo et al.), which are hereby incorporated by reference in its entirety.

To prepare the second aliquot of the blood sample for measurement, the method includes first mixing the second aliquot of the blood sample with a predetermined volume of the blood diluent, and subsequently adding a predetermined volume of the lytic reagent to lyse red blood cells. In the second sample mixture, remaining blood cells are essentially nucleated blood cells including white blood cells, and nucleated red blood cells if present in a clinical sample. The cell membranes of these nucleated blood cells are damaged by the lytic reaction, which result in substantially reduced cell volumes.

The population distribution of the nucleated blood cells is measured by a second direct current impedance (DC2) measurement in a non-focused flow aperture to obtain an one dimensional histogram. At the same time, the white blood cells can also be counted in the non-focused flow aperture by a third direct current impedance measurement.

The detection methods used for blood cell counting by a blood analyzer equipped with a DC impedance measurement device are generally described in U.S. Pat. No. 2,656,508 (to Wallace H. Coulter), which is hereby incorporated by reference in its entirety.

Figure 1C:
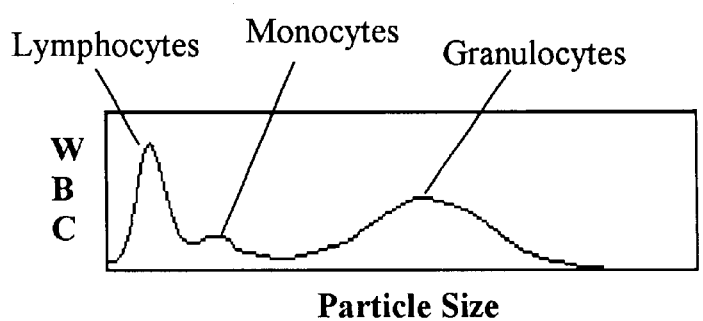
FIG. 1C is a DC2 histogram obtained from the measurement of the second aliquot of the same blood sample.

A differential analysis of the DC2 histogram can provide subpopulations of white blood cells. When ISOTON® III and LYSE S® III Diff are used for sample analysis, white blood cells are differentiated into three subpopulations, including lymphocytes, monocytes and granulocytes. FIG. 1C shows a histogram obtained from a normal blood sample processed and analyzed following the procedure described in Example 1. As shown, the white blood cells are differentiated into three subpopulations, importantly, no blood cell population appears on the left of lymphocytes. FIG. 2B shows a histogram obtained under the same condition from a clinical sample that has 5 NRBCs/100 WBC. It is apparent that NRBCs appear on the left of lymphocytes on the DC2 histogram.

Similar to the situation described previously with the first sample mixture, if lysed cell membranes in the second sample mixture are not dissolved sufficiently and below the second DC detection threshold at the time of measurement, they can also appear on the left extreme of the histogram. It is known that the second reagent system is stronger in terms of lysing potency, there are less instances where cell debris being measured with the nucleated blood cells. Additionally, since the first lysing reagent system and the second lysing reagent system have different chemistries and reaction mechanisms on blood cells, cell debris presents in the first sample mixture may not appear in the second sample mixture, and vice versa.

A first data analysis for analyzing NRBCs was performed on the blood cell distribution patterns obtained from the measurements of the first sample mixture. The analysis includes pattern recognitions of the blood cells in an individual measurement, and derivatives of the measurements, such as DC1, RF, Opacity (a function of RF and DC1), LS, RLS (a first transformed light scatter), and FLS (a second transformed light scatter). It also includes pattern recognitions of the blood cells in various combinations of two of the measurements and derivatives of the measurements, such as DC1 versus Opacity, DC1 versus RLS, and Opacity versus RLS. The analysis further includes a pattern recognition of the blood cells in a combination of the three measurements and derivatives of the measurements, such as a combination of DC1, Opacity and RLS, and a combination of DC1, Opacity and FLS.

The purpose of using derivatives, such as Opacity, RLS and FLS, is to improve population separation among blood cell subpopulations. The Opacity is defined as $(RF-85) \times 255/DC$. The RLS is defined as $(\log 10(LS)-2.2) \times 700000/(DC+2500)+50$. The FLS is defined as $(\log (LS+10)-2.5)/(DC+2500)^{1/2} \times 4480-70$.

The pattern recognition analysis produces numerous variables related to blood cell distribution patterns pertinent to the analysis of NRBCs. Typically, the variables include percentage of lymphocytes, mean channel of lymphocytes in DC1, Opacity and RLS, standard deviation of lymphocytes in DC1, Opacity and RLS, standard deviation of neutrophils in DC1, percentage of the cell debris cluster, mean channel of the cell debris cluster in DC1, Opacity and RLS, standard deviation of the cell debris cluster in DC1, Opacity and RLS, channel of the valley between the cell debris cluster and the white blood cells in DC1, ratio of the amplitude of the cell debris cluster to the amplitude of the valley between the cell debris cluster and the white blood cells, indication of the blood sample beyond 24 hours, and indication of the presence of a second lymphocyte population (described hereafter). Additional variables can also be generated in the first data analysis to facilitate differentiation of NRBCs from other cell types.

Based on analyses of various normal and clinical abnormal blood samples, particularly blood samples containing various amounts of NRBCs, a database is accumulated which comprises blood cell distribution statistics of the above described variables.

The first data analyses further differentiate the NRBCs from other cell types, particularly from lymphocytes, cell debris if present, and other cell populations which may appear in the same regions where NRBCs appear.

As shown in FIG. 2A, NRBCs are more closely positioned to lymphocytes in both DC1 and RLS axes than any other white cell subpopulations. It has been observed that for some abnormal blood samples, a group of lymphocytes having smaller cell sizes appear as a cluster under the normal lymphocyte population in DC1. This cluster of lymphocytes is also called low volume lymphocytes, or second lymphocyte population, for the purpose of the first data analysis. It is also known that lymphocytes of some patient samples, such as patients under chemotherapy, are more fragile, and they tend to overlyse and generate a cluster of partially lysed lymphocyte population, which also appear under the normal lymphocyte population in DC1. In both situations, the first data analysis analyzes the distribution patterns of both lymphocytes and NRBCs, and differentiates the second lymphocyte population from the NRBCs.

It is known that some clinical samples are more difficult to lyse. When lysed cell membranes in the sample mixture are not dissolved sufficiently and below the DC1 detection threshold at the time of measurement, they can also appear below the lymphocytes. However, it is found that cell debris has different distribution characteristics from that of NRBCs, which can facilitate differentiation of NRBCs from the cell debris.

A second data analysis for analyzing NRBCs was performed on the blood cell distribution obtained from the measurement of the second sample mixture. The analysis includes pattern recognitions of the blood cell distribution in DC2 histogram, which produces variables related to blood cell distribution patterns pertinent to the analysis of NRBCs. Typically the variables include the channels of the first peak and first valley in DC2 histogram, percentages of lymphocytes, and cell debris in DC2 histogram, the channel of lymphocyte peak in DC2 histogram, the channel and amplitude of the valley between cell debris and lymphocytes in DC2 histogram, ratio of the lymphocyte peak amplitude to the amplitude of the valley between lymphocytes and cell debris, amplitude of the first channel in DC2 histogram, the ratio of the amplitude of the first peak in DC2 to the amplitude of the first channel in DC2, and the separation between lymphocytes and cell debris in DC2 histogram. Additional variables can also be generated in the second data analysis to facilitate differentiation of NRBCs from other cell types.

In a similar manner to the first data analysis, based on analysis of various normal and clinical abnormal blood samples, particularly blood samples containing various amounts of NRBCs, a second database is accumulated which includes blood cell distribution statistics of the DC2 histogram.

The second data analysis also further differentiates the NRBCs from other cell types, particularly lymphocytes. It is noted that DC1 and DC2 have substantially different scales. As described previously, under normal circumstances lymphocytes in the first sample mixture are intact, and in their near native states. In the second sample mixture, membranes of lymphocytes are lysed, or partially lysed. As shown in FIG. 2B, the NRBCs are closer to lymphocytes in DC2 than DC1. Therefore, it is important to differentiate NRBCs from the lymphocytes on the DC2 histogram.

Following the first and the second data analysis, the method of the present invention performs a combined analysis. The combined analysis combines the analysis results obtained from the first and the second data analysis, and generates a profile for the blood sample under analysis. The profile includes all above-described variables generated in the first and second data analysis, which contains composite cell population distribution patterns pertinent to NRBC analysis. A combined database is accumulated from a large number of normal and clinical abnormal blood samples, which contains various cell distribution statistical information. The combined analysis further performs a pattern recognition analysis on the profile of the blood sample. Based on the blood cell distribution statistics the combined analysis then further differentiates NRBCs from other cell types, and obtains the amount of NRBCs present in the blood sample.

It is apparent from the previously discussions of the individual data analyses that either first and second data analysis can face interferences from cell debris, or other cell types such as aged blood cells, platelet clumps and giant platelet, if their sizes coincide with NRBCs in the sample mixtures under analysis. In addition, it is known that NRBCs have a wide size distribution depending on maturity of the cells, and the lymphocytes can also have a wider distribution in abnormal blood samples. All above described situations can complicate one or the other individual data analysis, and cause errors in the analysis of NRBCs if the method is based on only one of them. However, the combined analysis overcomes the deficiencies of individual analysis, and enables a quantitative analysis of NRBC population in the blood sample.

It is important to understand that the lysing reactions involved in preparing the first sample mixture and the second sample mixture are substantially different. The method of the present invention takes advantages of the differences by combining the two individual data analysis. It has been found that the cell debris present in the first sample mixture related to the response of the blood cells to the first lysing reagent system often not present in the second sample mixture. In this situation, the interference present from the first data analysis can be removed in the combined analysis. On the other hand, the interference of aged blood cells, platelet clumps and giant platelet to the differentiation of NRBCs in the second sample mixture based on the DC2 histogram may not cause interference in the first data analysis. Hence, the interference can be removed in the combined analysis.

Example 3 and 4 illustrate the function of the combined analysis. In each case, the combined analysis reduced the uncertainties or interferences present in the individual analyses, and provided true positive NRBC flags, and the concentrations of NRBCs consistent with the manual reference method.

The analysis result of the instant method can be reported as a flagging of the presence of NRBCs in a blood sample, and as a concentration of NRBCs in the blood sample. The concentration of NRBCs can be reported as number of NRBCs per hundred of white blood cells (NRBC/100 WBC), which is the same unit as the manual reference method, or as numbers of NRBCs in per unit volume of a blood sample. To report the absolute count, the concentration of white blood cells measured by the third DC impedance measurement is used, and the total dilution used in the sample preparation is also corrected.

As described previously, NRBCs present in a blood sample can elevate white blood cell count, and cause erroneous white blood cell count results. With the method of the present invention, the interference of NRBCs can be corrected from the white blood cell count.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

On a COULTER® GEN*S™ hematology analyzer, a first aliquot of an EDTA-anticoagulated fresh normal whole blood sample was aspirated and mixed with a volume of Erythrolyse II in a mixing chamber to lyse the red blood cells, and subsequently mixed with a volume of StabiLyse to retard further lytic reaction in this first sample mixture. The first sample mixture was delivered to a focused flow cell with a sheath fluid, ISOTON® III diluent. The Erythrolyse™ II, StabiLyse™, and ISOTON® III diluent are products of Beckman Coulter, Inc., Miami, Fla.

The first sample mixture was measured in the focused flow cell by a detector which included a first direct current impedance (DC1) measurement means, a radio frequency impedance (RF) measurement means, and a light scatter measurement (LS) means. The light scatter measurement means detects median angle light scatter signals from about 10° to about 70°.

During the same time period that the first aliquot of a blood sample was processed and measured, a second aliquot of the same blood sample was aspirated and diluted with ISOTON® III diluent in a WBC bath, and subsequently mixed with a second lytic reagent, LYSE S® III Diff (a product of Beckman Coulter, Inc., Miami, Fla.) The second sample mixture was induced by vacuum to a non-focused aperture embedded in the WBC bath. A second direct current impedance measurement (DC2) was performed in the non-focused aperture to obtain a blood cell distribution of nucleated blood cells.

At the same time of the DC2 measurement, the white blood cells in the second sample mixture were enumerated in the non-focused aperture by a third direct current impedance measurement. The white blood cell count (WBC) was reported as numbers of white blood cells in per unit volume of the blood sample. All sample processes and measurements described above were performed following the instrument operation manual.

The obtained measurements from the first aliquot blood sample in DC1, RF and LS were used to construct a three-dimensional scatter plot. FIG. 1A shows a two-dimensional projection (scaftergram) of the three-dimensional scatter plot. In FIG. 1A, the vertical axis is DC1, and the horizontal axis is RLS, a first transformed LS, which is a function of DC1 and LS. FIG. 1B shows another two-dimensional projection of the three-dimensional scatter plot. In FIG. 1B, the vertical axis is DC1, and the horizontal axis is Opacity (OP), which is a function of DC1 and RF. FIGS. 1A and 1B illustrate differentiation of white blood cell subpopulations including lymphocytes, monocytes, neutrophils, eosinophils, and basophils.

As shown, in a region below lymphocytes in both two-dimensional scattergrams no blood cell population presented there. For the properly lysed blood sample, no cell debris showed in the scattergrams either.

The DC2 measurement of the second aliquot of the blood sample was used to construct an one-dimensional histogram, as shown in FIG. 1C. The white blood cells were differentiated into three subpopulations, including lymphocytes, monocytes and granulocytes. As shown, on the left of the lymphocytes no blood cell population appeared in that region. For the properly lysed blood sample, no cell debris showed in the histogram.

EXAMPLE 2

A clinical whole blood sample containing 5 NRBCs/100 WBC was processed using the same reagents and procedure described in Example 1, and measured on a COULTER® GEN*S instrument under the same conditions. The NRBC concentration was obtained from a 100 cell manual count provided by the hospital.

FIGS. 2A and 2B are the obtained DC1 versus RLS, and DC1 versus Opacity scattergram. As shown, the NRBCs appeared in the region below the lymphocytes. FIG. 2B is the obtained DC2 histogram, and the NRBCs appeared in the region on the left of lymphocytes.

EXAMPLE 3

Figure 3A:
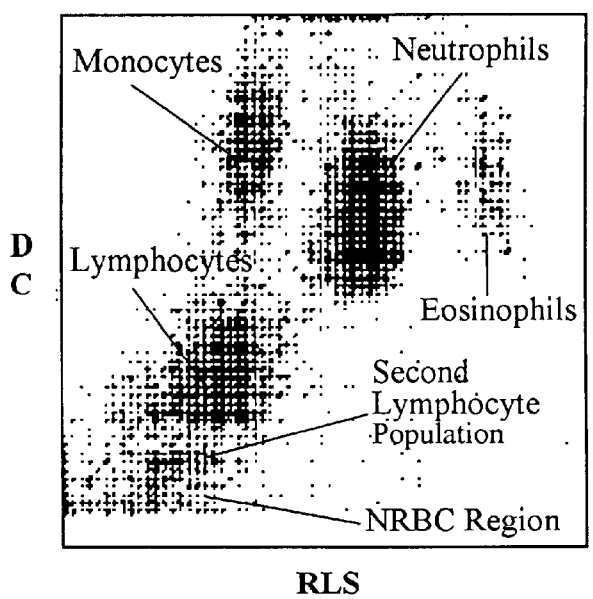
FIGS. 3A and 3B are the scattergrams obtained from the measurement of the first aliquot of a clinical blood sample containing NRBCs as described in Example 3.
Figure 3B:
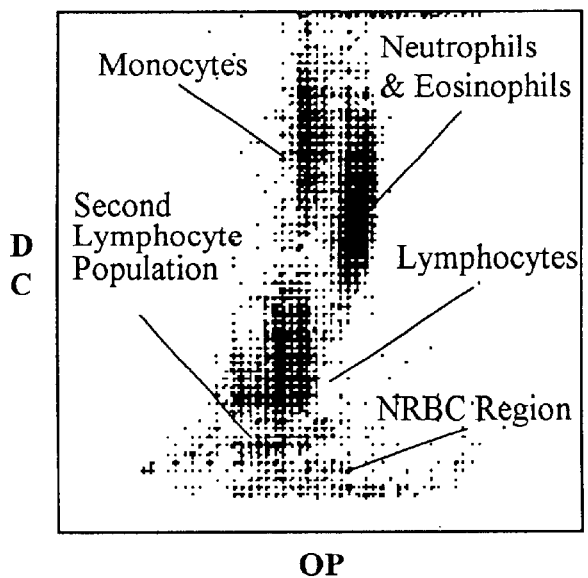
Figure 3C:
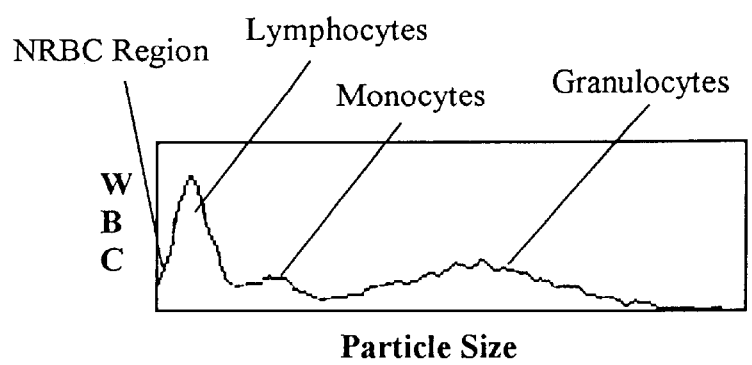
FIG. 3C is a DC2 histogram obtained from the measurement of the second aliquot of the same clinical sample.

A clinical whole blood sample containing 13 NRBCs/100 WBC was processed using the same reagents and procedure described in Example 1, and measured on a COULTER® GEN*S instrument under the same conditions. FIGS. 3A and 3B are the obtained DC1 versus RLS, and DC1 versus Opacity scattergrams, respectively. As shown, there was a second lymphocyte cluster underneath the normal lymphocyte in DC1, and NRBCs appeared in the region below the second lymphocyte cluster. FIG. 3C is the obtained DC2 histogram. In this case, the lymphocyte population extended into NRBC region, therefore, there was no separation between lymphocytes and NRBCs in the DC2 histogram.

For this clinical sample, both the first and the second data analysis indicated the presence of NRBCs. The second data analysis was not able to enumerate the NRBCs because of lacking separation between the lymphocytes and NRBCs. However, the first data analysis was able to differentiate the NRBCs from other cell types. The combined analysis reported 13 NRBCs/100 WBC, which was consistent with the manual reference report.

EXAMPLE 4

Figure 4A:
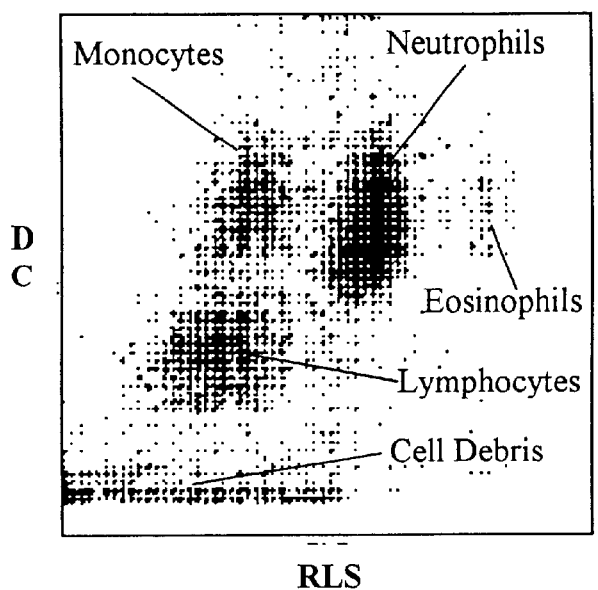
FIGS. 4A and 4B are the scattergrams obtained from the measurement of the first aliquot of a clinical blood sample as described in Example 4.
Figure 4B:
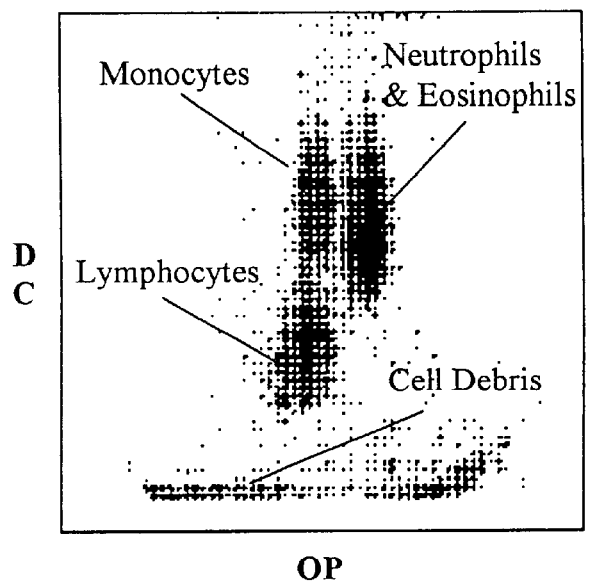
Figure 4C:
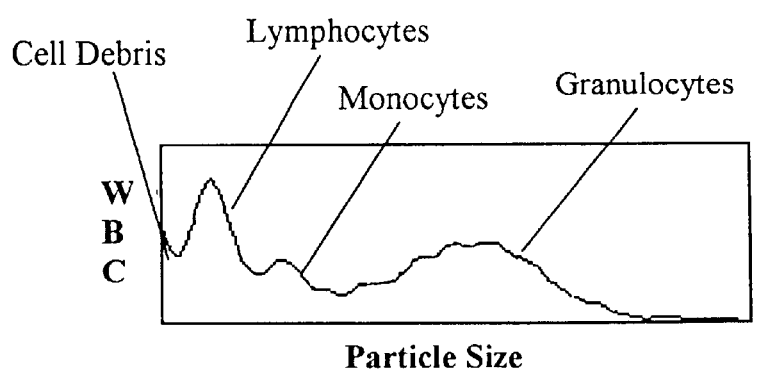
FIG. 4C is a DC2 histogram obtained from the measurement of the second aliquot of the same clinical sample.

A clinical whole blood sample was processed using the same reagents and procedure described in Example 1, and measured on a COULTER® GEN*S instrument under the same conditions. FIGS. 4A and 4B are the obtained DC1 versus RLS, and DC1 versus Opacity scattergrams, respectively. FIG. 4C is the obtained DC2 histogram. For this blood sample, the second data analysis was not determinative of the presence of NRBCs. However, as shown in FIG. 4A there was a dense cell debris cluster which had a very low DC1 value and small standard deviation in DC1. It has been found that this type of cell debris distribution characteristics usually does not correlate to the presence of NRBCs in a blood sample, which is consistent with the observation that NRBCs tend to have a wide size distribution. The combined analysis confirmed no NRBCs for this blood sample, which was consistent with the manual reference report.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A method of analyzing nucleated red blood cells in a blood sample comprising:
   (a) exposing a first aliquot of a blood sample to a first lysing reagent system to lyse red blood cells and to form a first sample mixture,
   (b) exposing a second aliquot of said blood sample to a second lysing reagent system to lyse red blood cells and to form a second sample mixture,
   (c) measuring said first sample mixture in a flow cell by a detection comprising a first direct current impedance measurement (DC1), radio frequency impedance measurement (RF), and light scatter measurement (LS),
   (d) measuring blood cell distributions of said second sample mixture by a second direct current impedance measurement (DC2),
   (e) analyzing blood cell distribution patterns obtained from measuring said first sample mixture, and differentiating nucleated red blood cells from other cell types,
   (f) analyzing blood cell distribution patterns obtained from measuring said second sample mixture, and differentiating nucleated red blood cells from other cell types,
   (g) performing a combined analysis on a profile obtained by combining results of analysis from step (e) and (f), said combined analysis further differentiating nucleated red blood cells from other cell types, and
   (h) reporting nucleated red blood cells in said blood sample.

2. The method of claim 1, wherein said reporting nucleated red blood cells comprises reporting the presence of nucleated red blood cells in said blood sample.

3. The method of claim 1, wherein said reporting nucleated red blood cells comprises reporting numbers of nucleated red blood cells per hundred white blood cells in said blood sample.

4. The method of claim 1, wherein said measuring blood cell distributions of said second sample mixture by a second direct current impedance measurement (DC2) is performed in a non-focused flow aperture.

5. The method of claim 4 further comprising counting remaining blood cells in said second sample mixture in said non-focused flow aperture by a third direct current impedance measurement, and reporting numbers of white blood cells in an unit volume of said blood sample.

6. The method of claim 5 further comprising reporting an amount of nucleated red blood cells as numbers of nucleated red blood cells in an unit volume of said blood sample.

7. The method of claim 6, wherein measuring blood cell distributions of said second sample mixture by a second direct current impedance measurement (DC2) and counting remaining blood cells in said second sample mixture by a third direct current impedance measurement are performed simultaneously in said non-focused flow aperture.

8. The method of claim 1, wherein said detection comprising a first direct current impedance measurement (DC1), radio frequency impedance measurement (RF), and light scatter measurement (LS) of said first sample mixture is performed simultaneously.

9. The method of claim 8, wherein said light scatter measurement is performed using median angle of light scatter signals.

10. The method of claim 9, wherein said median angle light scatter signals are in a range from about 10 degree to about 70 degree.

11. The method of claim 1, wherein said analyzing blood cell distribution patterns obtained from measuring said first sample mixture comprises analyzing blood cell distribution patterns obtained from each of said measurements and derivatives of said measurements, in a plurality of combinations of two of said measurements and derivatives of said measurements, and in at least one combination of three of said measurements and derivatives of said measurements.

12. The method of claim 11, wherein said measurements and derivatives of said measurements comprise DC1, RF, Opacity (a function of RF and DC1), LS, RLS (a first transformed light scatter), and FLS (a second transformed light scatter).

13. The method of claim 11, wherein said combinations of two measurements and derivatives of said measurements comprise DC1 versus Opacity (a function of RF and DC1), DC1 versus RLS (a first transformed light scattes), and Opacity versus RLS.

14. The method of claim 11, wherein said at least one combination of three said measurements and derivatives of said measurements comprises a combination of DC1, Opacity (a function of RF and DC1) and RLS (a first transformed light scatter), and a combination of DC1, Opacity and FLS (a second transformed light scattter).

15. The method of claim 11, wherein said analyzing blood cell distribution patterns obtained from measuring said first sample mixture further comprises differentiation of five white blood cell subpopulations comprising lymphocytes, monocytes, neutrophils, eosinophils and basophils.

16. The method of claim 1, wherein said analyzing blood cell distribution patterns obtained from measuring said second sample mixture further comprises differentiating three white blood subpopulations comprising lymphocytes, monocytes, and granulocytes.

17. The method of claim 1, wherein said first lysing reagent system comprises a lytic reagent, and a stabilizing reagent.

18. The method of claim 1, wherein said second lysing reagent system comprises a blood diluent, and a lytic reagent.

19. A method of enumerating nucleated red blood cells in a blood sample comprising:
   (a) exposing a first aliquot of a blood sample to a first lysing reagent system to lyse red blood cells and to form a first sample mixture,
   (b) exposing a second aliquot of said sample to a second lysing reagent system to lyse red blood cells and to form a second sample mixture, (c) measuring said first sample mixture in a flow cell by a detection comprising a first direct current impedance measurement (DC1), radio frequency impedance measurement (RF), and light scatter measurement (LS), (d) measuring blood cell distributions of said second sample mixture by a second direct current impedance measurement (DC2) in a non-focused flow aperture, (e) analyzing blood cell distribution patterns obtained from measuring said first sample mixture, and differentiating nucleated red blood cells from other cell types, (f) analyzing blood cell distribution patterns obtained from measuring said second sample mixture, and differentiating nucleated red blood cells from other cell types, (g) performing a combined analysis on a profile obtained by combining results of analysis from step (e) and (f), said combined analysis further differentiating nucleated red blood cells from other cell types, and (h) reporting numbers of nucleated red blood cells per hundred white blood cells.

* * * * *